(12) United States Patent
Lee et al.

(10) Patent No.: US 6,887,458 B1
(45) Date of Patent: May 3, 2005

(54) VASCULAR EMBOLIC MATERIALS HAVING MULTIFUNCTIONS

(75) Inventors: Kyu-Ho Lee, 7-201 Hyundai Villa, 172 Sangil-dong, Kangdong-ku, Seoul 134-090 (KR); Kyung-Chae Kim, Kumi-shi (KR)

(73) Assignee: Kyu-Ho Lee, Seoul (KR)

( * ) Notice: Subject to any disclaimer, the term of this patent is extended or adjusted under 35 U.S.C. 154(b) by 0 days.

(21) Appl. No.: 09/959,695

(22) PCT Filed: May 3, 2000

(86) PCT No.: PCT/KR00/00420

§ 371 (c)(1),
(2), (4) Date: Nov. 5, 2001

(87) PCT Pub. No.: WO00/66183

PCT Pub. Date: Nov. 9, 2000

(30) Foreign Application Priority Data

May 3, 1999 (KR) ......................... 1999-15941

(51) Int. Cl.⁷ .......................... A61B 5/055; A61K 9/00; A61K 49/00; A61K 9/14
(52) U.S. Cl. ..................... 424/9.322; 424/400; 424/489
(58) Field of Search .......................... 424/400

(56) References Cited

U.S. PATENT DOCUMENTS 5,443,478 A * 8/1995 Purdy .......................... 606/200
5,716,981 A * 2/1998 Hunter et al. ................ 514/449
5,851,508 A * 12/1998 Greff et al. ............... 424/9.411
5,886,026 A 3/1999 Hunter et al.
6,015,541 A 1/2000 Greff et al.

FOREIGN PATENT DOCUMENTS

| JP | 50-969 | 1/1975 |
| JP | 5-969 | 1/1983 |
| JP | 63-29542 | 2/1988 |
| JP | 6-329542 | 11/1994 |
| WO | WO 99/12577 | 3/1999 |

* cited by examiner

*Primary Examiner*—James Spear
*Assistant Examiner*—Retford Berko
(74) *Attorney, Agent, or Firm*—Oblon, Spivak, McCleeland, Maier & Neustadt, P.C.

(57) ABSTRACT

The present invention relates to a vascular embolic material for use in the treatment of an angiotropy of various tumors and a vascular malformation. Specifically, the present invention relates to a vascular embolic material having the specific morphological, physicochemical and radiological characteristics and multifunction in the form of a bead or a sponge comprising a mixture of a hydrophilic polymer material and a metal material. The specific physicochemical and radiological characteristics of the vascular embolic material according to the present invention facilitate its clinical use and aid in the diagnosis before and after the embolization. Further, a local radiation treatment and anticancer treatment is possible and thus the therapeutic effect on said disorders can be enhanced.

9 Claims, 7 Drawing Sheets

*Sponge form*

*Bead form*

PVA, 100 X LM

VASCULAR EMBOLIC MATERIALS HAVING MULTIFUNCTIONS

BACKGROUND OF THE INVENTION

1. Field of the Invention

The present invention relates to a vascular embolic material for use in the treatment of an angiotropy of various tumors and a vascular malformation. Specifically, the present invention relates to a vascular embolic material having the specific morphological, physicochemical and radiological characteristics and multifunction in the form of a bead or a sponge comprising a mixture of a hydrophilic polymer material and a metal material.

2. Description of the Prior Art

Various vascular embolic materials are generally used to block an angiotropy or vascular malformation by infusing them via a fine vascular catheter while subjecting to angiography.

Various kinds of materials that are harmless to the human body and that which do not bring about adverse reactions are selected and used as a vascular embolic material depending on the purposes. However, it is now required in clinical therapeutics for the materials to have the deliverability of a specific drug, a radioactive isotope, etc., to a local region as the capability to block blood vessels.

SUMMARY OF THE INVENTION

It is, therefore, an object of the present invention to provide a new vascular embolic material having multifunction in the form of a bead or a sponge, which is harmless to the human body, hydrophilic and substantially permanent and moreover has the specific morphological, physicochemical and radiological characteristics and the deliverability of a specific drug and a radioactive isotope.

DETAILED DESCRIPTION OF THE INVENTION

The object of the present invention is established by a vascular embolic material having multifunction in the form of a bead or a sponge comprising a mixture of a hydrophilic polymer material and a metal material.

Therefore, the present invention is directed to a vascular embolic material having multifunction in the form of a bead or a sponge comprising a mixture of a hydrophilic polymer material and a metal material.

According to the present invention, polyvinyl alcohol is primarily used as the polymer material constituting the vascular embolic material. Polyvinyl alcohol having a molecular weight of 50,000 to 300,000 is preferably used. The metal material is preferred from the group consisting of $TiO_2$, Pt or a mixture of $TiO_2$ and Pt. The mixing ratio of the polymer material and the metal material should preferably be 4–10:1.

The characteristics of the vascular embolic material according to the present invention will be described in greater detail in the following section.

Morphological Characteristics

Figure 1A:
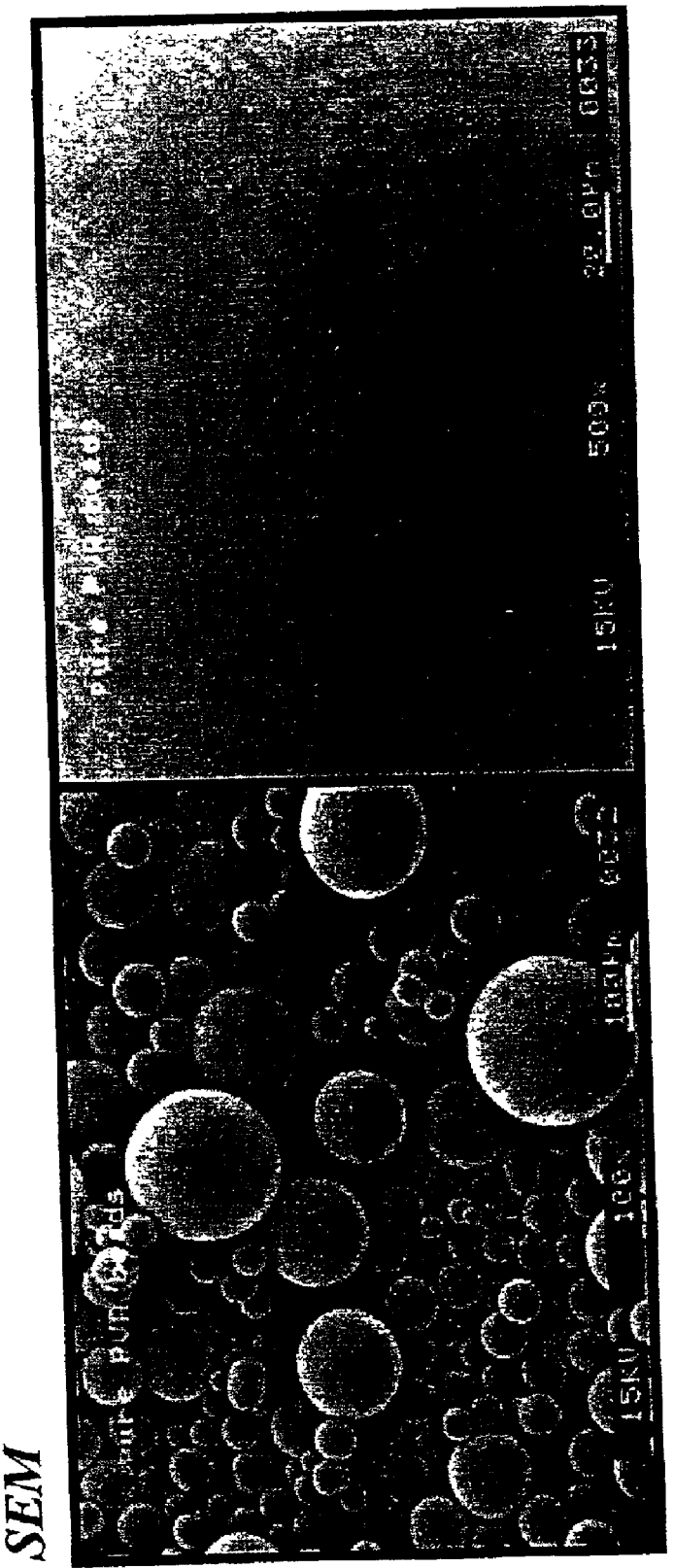
FIGS. 1a and 1b are drawings showing polyvinyl alcohol materials in the form of a bead and a sponge, respectively.
Figure 1B:
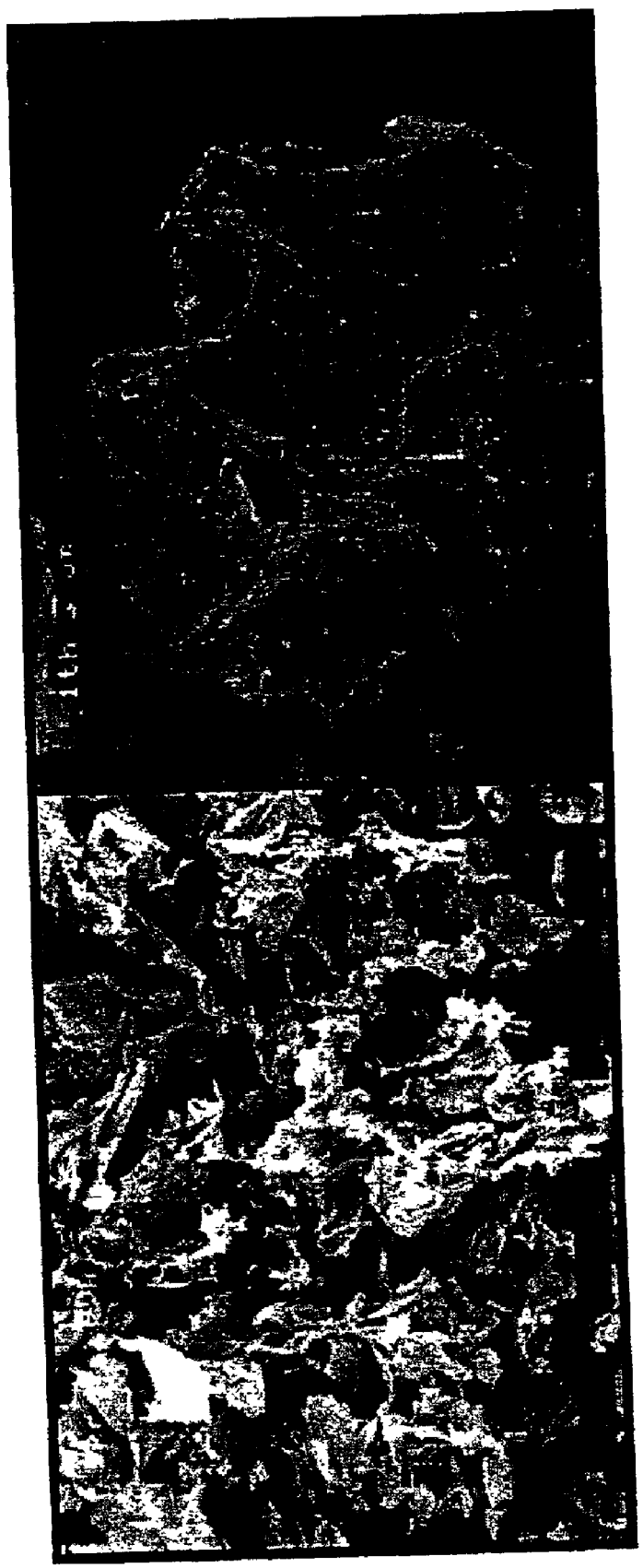
Figure 2A:
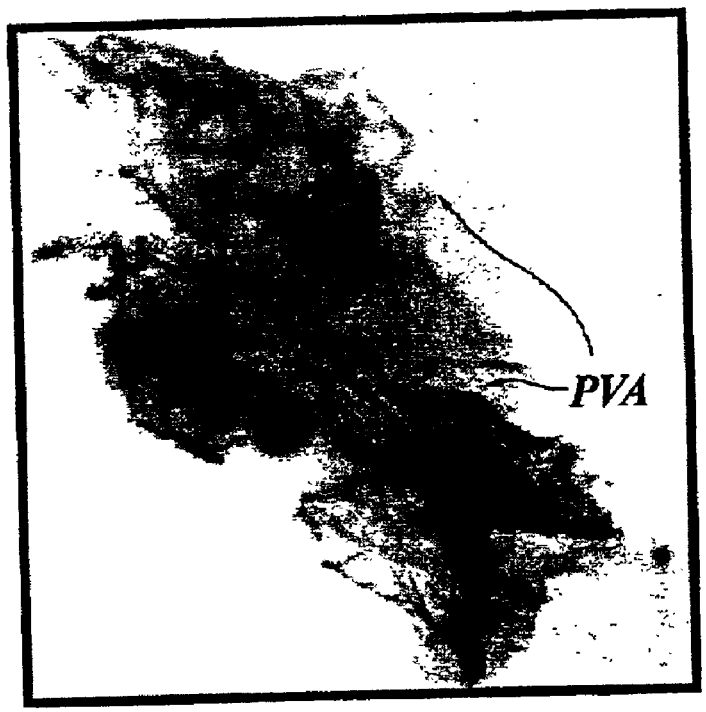
FIGS. 2a and 2b are drawings showing the new vascular embolic materials in the form of a bead or a sponge, respectively.
Figure 2B:
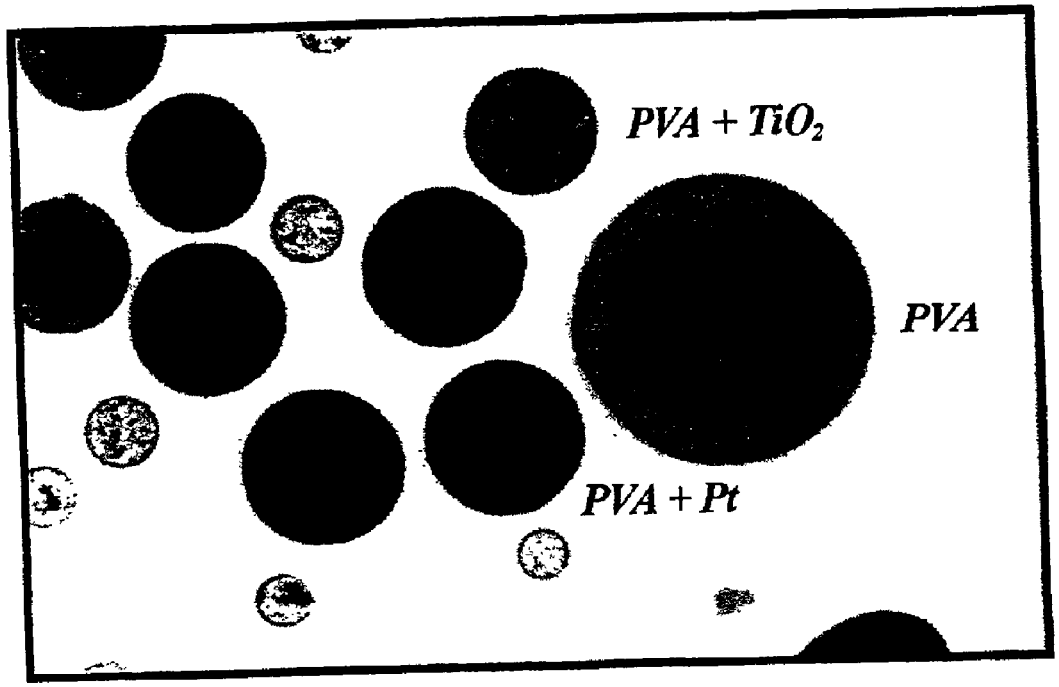

The vascular embolic material according to the present invention has either a bead or a sponge form, as shown in FIGS. 2a and 2b. Such vascular embolic material may be prepared in various sizes of 10 to 1000 μm and easily infused into a very fine vascular catheter.

Figure 3:
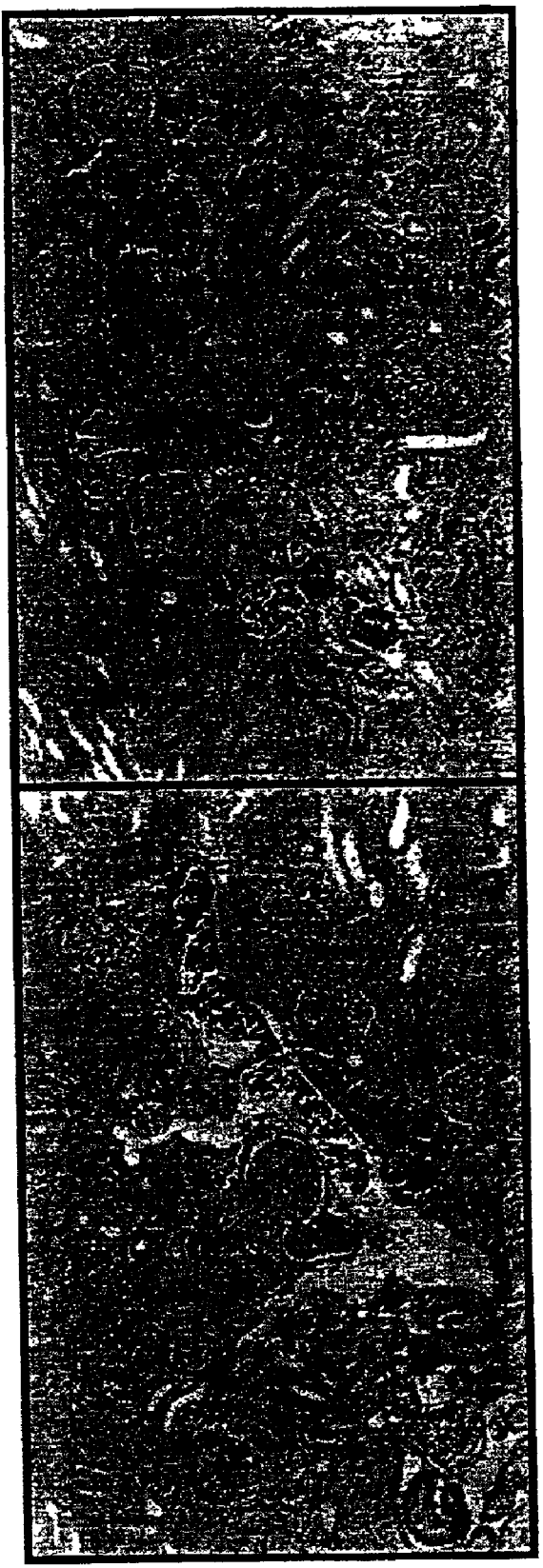
FIG. 3 is a drawing showing the result from a vascular embolization of a kidney of a rabbit.

The result from a vascular embolization of a kidney of a rabbit (a pre-animal test) is shown in FIG. 3.

Physicochemical Characteristics

The vascular embolic material according to the present invention is prepared using polyvinyl alcohol, with a molecular weight of 50,000 to 300,000, as a polymer material and $TiO_2$ (99.95% of purity), Pt (99.9999% of purity) or a mixture of $TiO_2$ and Pt having a size of 0.02 to 2 μm. Such vascular embolic material has a specific gravity of 1.2 to 2.5, has a strong hydrophilicity and is harmless to the human body.

Radiological Characteristics

Most vascular embolic materials currently used cannot be clearly recognized after the embolization since they appear transparent to radiation (X-ray).

Figure 4:
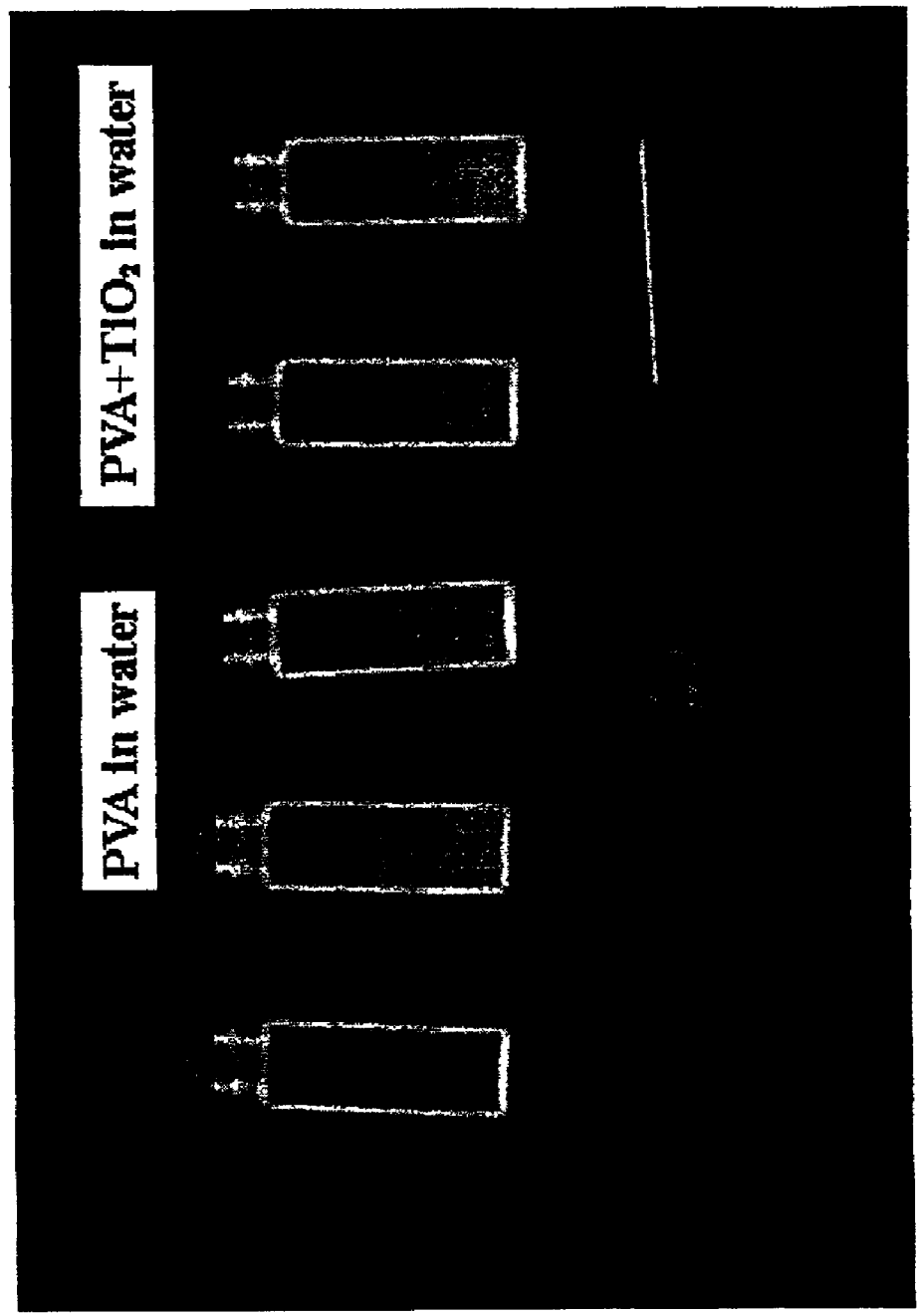
FIG. 4 is an X-ray photographic image of a mixture of polyvinyl alcohol and $TiO_2$.

However, the vascular embolic material according to the present invention includes a metal material that is visible to X-ray and thus the position can be seen. Therefore, the vascular embolic material according to the present invention shows an opaque image in an X-ray photography (see FIG. 4).

Figure 5:
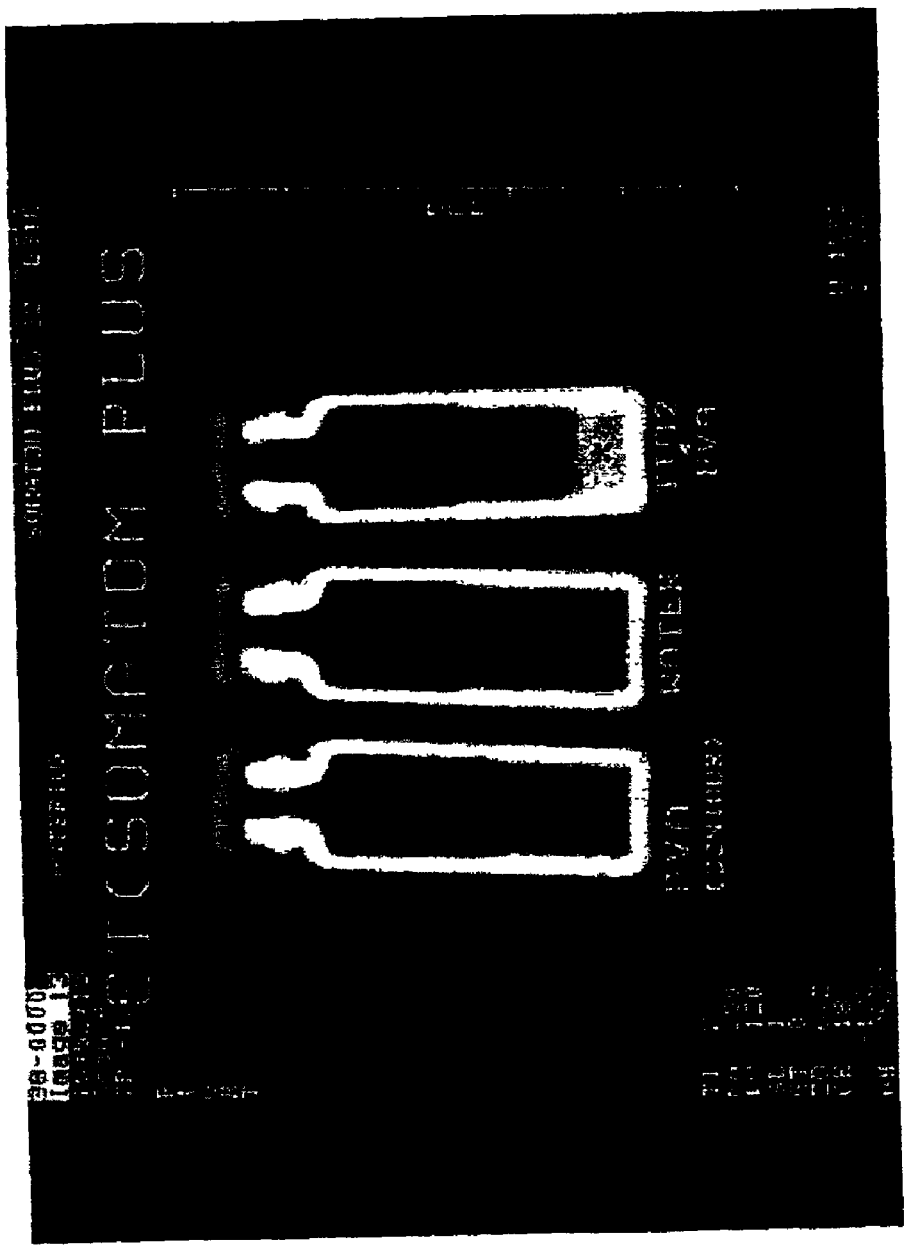
FIG. 5 is a CT photographic image of a mixture of polyvinyl alcohol and $TiO_2$.
Figure 6:
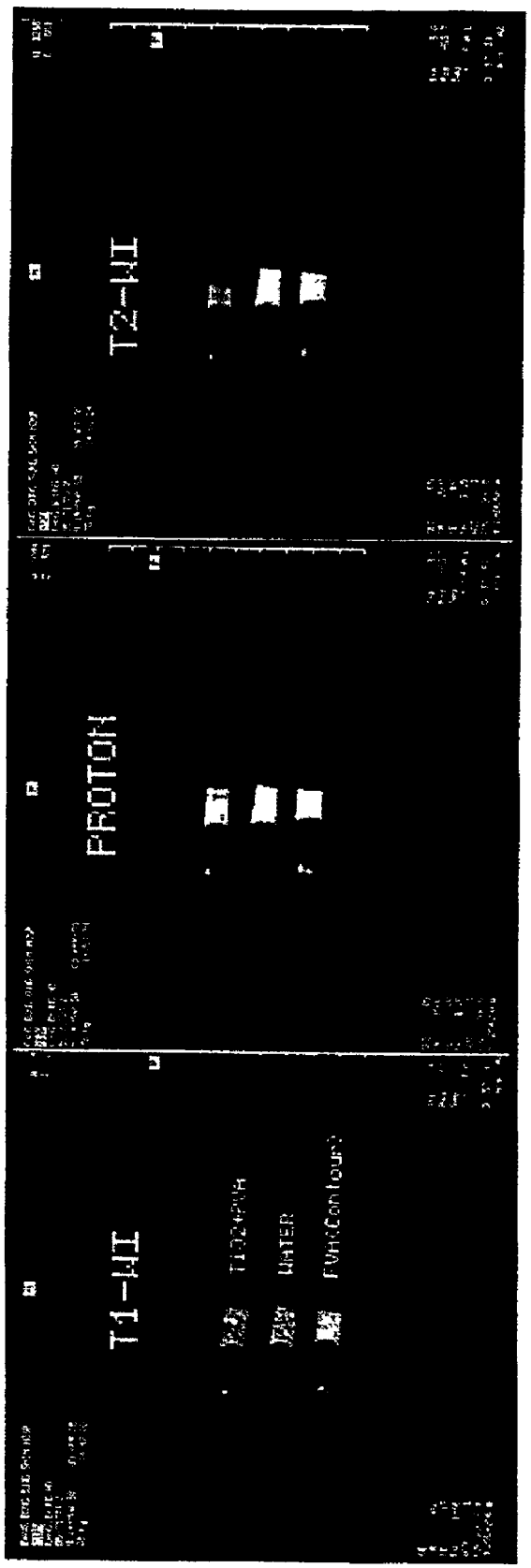
FIG. 6 is an MRI photographic image of a mixture of polyvinyl alcohol and $TiO_2$.

Also, the vascular embolic material according to the present invention shows a high-density image in a computerized tomography (see FIG. 5). Further, such vascular embolic material does not affect an image during a magnetic resonance imaging and shows a low resonance image (see FIG. 6).

Multifunctionality

An irradiation and an anticancer agent are generally used to treat a tumor. In order to enhance the therapeutic effect and reduce the possibility of an adverse reaction to the whole body, an irradiation of a radiation or infusion of an anticancer agent on a local legion is carried out in clinical therapeutics.

The vascular embolic material according to the present invention has an embolization effect of blocking an angiotropy. Further, such vascular embolic material may itself become isotoped by isotoping a metal material and thus having the deliverability of β-ray and γ-ray useful for the treatment. In addition, it is possible to add a drug such as an anticancer agent to the vascular embolic material to enhance the therapeutic effect on a local legion.

The vascular embolic material according to the present invention may be prepared by a method for drying in oil or a freeze drying method.

PREFERRED EMBODIMENT OF THE INVENTION

The present invention will be described in greater detail by way of the following examples, which are not intended to limit the invention.

EXAMPLE 1
Preparation of the Vascular Embolic Material in the Form of a Bead by a Method for Drying in Oil 7% by weight of polyvinyl alcohol and 0.5 to 1.75% by weight of Pt or $TiO_2$ powder were placed on a tertiary distilled water in a beaker while stirring at 700 rpm for 30 minutes. The solution was gradually heated from 30° C. to 80° C. while stirring for 2 to 3 hours and increasing the stirring speed to 1000 rpm in order to completely dissolve polyvinyl alcohol. Then, the solution was sealed and left for 12 hours or so at room temperature to remove the bubbles therein.

0.3% by weight of sorbitan monostearate as a surfactant was added to 1 kg dispersion of liquid paraffin and gradually heated from room temperature to 70° C. and stirred at 1200 rpm. The mixed solution of polyvinyl alcohol and a metal material (Pt or $TiO_2$) was infused into the stirred liquid by a syringe to make it a fine drop state. The dispersion was heated in a bath at 95° C. to 110° C. for 4 hours to gradually dry the drop and to prepare a mixture of polyvinyl alcohol and a metal in the form of a bead. The mixture was filtered out while maintaining the temperature of 60±5° C., repeatedly washing with n-hexane and drying under the reduced pressure. The dried materials were classified by size through a sieve.

Polyvinyl alcohol and a metal material were mixed so as that the ratio of the solid components is 4:1. When two kinds of metal materials were used together, the ratio between the two was varied depending on the purposes but the total amount between polyvinyl alcohol and a metal material was kept the same. Even the vascular embolic material in the form of a bead was prepared with polyvinyl alcohol only, the amount of polyvinyl alcohol was 8% by weight and an anticancer agent was further added at an adequate amount.

EXAMPLE 2
Preparation of the Vascular Embolic Material in the Form of a Sponge by a Freeze Drying Method A mixed solution of polyvinyl alcohol and a metal material was prepared by the same method, as described in example 1. An equivalent amount of ammonium bicarbonate $[(NH_4)_2CO_3]$ was added to the solution at room temperature so as that the ratio of the solid components is 1:1, and was mixed well. The bubbles formed at room temperature in vacuum state ($10^3$ torr). The vessel was frozen by quenching with liquid nitrogen to −170° C. and this state was maintained for 10 minutes. It was confirmed that the materials in the vessel were completely frozen. Liquid nitrogen was removed and then moisture was further removed in vacuum state for 30 minutes. Thereafter, additionally moisture was removed by dipping into a mixed solution of an ice water and salt in vacuum state at −10° C. for 1 hour. After drying at room temperature in vacuum state for 4 hours, the resultant was dried again in a water bath at 50° C. for 1 hour to completely remove moisture. Finally, liquid nitrogen was placed in the vessel and the materials in the vessel were pulverized and classified by size through a sieve.

Even when only polyvinyl alcohol was used without adding a metal material, the component ratio to ammonium bicarbonate was maintained in 1:1. An anticancer agent was further added in an adequate amount.

EXAMPLE 3
Isotoping of the Vascular Embolic Material According to the Present Invention A metal material included in the vascular embolic material according to the present invention was irradiated in the core of a nuclear reaction (Hanaro) and a region where neutrons were generated in $1.7×10^{13}/cm^2/sec$ for 1 minute and 10 minutes. β-ray and γ-ray emitted from the material was determined by a neutron activation analysis using Multi-Channel Detector and thus isotoping was confirmed.

The results are shown in Table 1.

TABLE 1

| Polyvinyl alcohol + $TiO_2$ + Pt(2), after (n, gamma) reaction, NAA | | | | |
|---|---|---|---|---|
| Elements | Concentration | Radioneuclides | β-ray | γ-ray |
| Ti | 11.60% | Ti-51 | 1.56 MeV (8%) | 0.32 MeV (93%) |
|  |  |  | 2.17 MeV (92%) | 0.61 MeV (1.2%) |
|  |  |  |  | 0.93 MeV (4.9%) |
| Pt | 3.13 | Pt-199 | in-progress |  |
| Na | 0.56 | Na-24 | in-progress |  |
| Cl | 563 ppm | Cl-38 | in-progress |  |
| Al | 130 | Al-28 | in-progress |  |
| V | 1.5 | V-52 | in-progress |  |

EXAMPLE 4
Anticancer Effect of the Vascular Embolic Material According to the Present Invention 5 to 50 mg of cisplastin among anticancer agents was added to the vascular embolic material according to the present invention and applied to a cultured cancerous cell. Then the anticancer effect was determined.

The results using 23.98 mg of cisplatin (NAA) are set forth in Table 2.

TABLE 2

| Elements | Radioisotope | $T_{1/2}$ | Concentration |
|---|---|---|---|
| Pt | Pt-195 m | 96.48 hr | 6.22 ± 0.06% |
| Au | Au-198 | 64.80 | 6.42 ± 0.02 ppm |
| Na | Na-24 | 15.0 | 2.67 ± 0.15% |
| Cl | Cl-38 | 37.7 min | 3.69 ± 0.02% |

According to the present invention, a vascular embolic material for use in the treatment of a tumor and a vascular malformation is provided. The specific physicochemical and radiological characteristics of the material according to the present invention facilitate its clinical use and aid in the diagnosis before and after the embolization. Further, a local radiation treatment and anticancer treatment is possible and thus the therapeutic effect on said disorders can be enhanced.

What is claimed is:

1. A vascular embolic material having multifunction in the form of a bead comprising a mixture of a polyvinyl alcohol and a metal material, wherein the metal material is isotoped by a neutron radiation and is selected from the group consisting of Pt and a mixture of Pt and $TiO_2$, and the mixing ratio of the polyvinyl alcohol hydrophilic polymer material and the metal material is 4–10:1.

2. The vascular embolic material according to claim 1, wherein the polyvinyl alcohol has a molecular weight of 50,000 to 300,000.

3. The vascular embolic material according to claim 1 further comprising a drug.

4. The vascular embolic material according to claim 3, wherein the drug is tumoricidal or anticancer agent.

5. The vascular embolic material according to claim 1, wherein the metal material is a mixture of Pt and $TiO_2$.

6. The vascular embolic material according to claim 1, consisting of a mixture of a polyvinyl alcohol, a metal material and an anticancer agent.

7. The vascular embolic material according to claim 6, wherein the anticancer agent is a cisplastin anti-cancer agent.

8. The vascular embolic material according to claim 1, wherein the metal is dispersed in the polyvinyl alcohol.

9. The vascular embolic material of claim 1, wherein the neutron radiation is carried out for from 1 to 10 minutes in a nuclear reactor core generating neutrons at $1.7 \times 10^{13}/cm^2/sec$.

* * * * *